US006497949B1

(12) United States Patent
Hyde et al.

(10) Patent No.: US 6,497,949 B1
(45) Date of Patent: Dec. 24, 2002

(54) ADHESIVE BLENDS COMPRISING HYDROPHILIC AND HYDROPHOBIC PRESSURE SENSITIVE ADHESIVES

(75) Inventors: Patrick D. Hyde, Burnsville, MN (US); Anthony R. Clanton, Woodbury, MN (US); Melinda B. Gieselman, Eagan, MN (US); Jingjing Ma, Woodbury, MN (US); Robert H. Menzies, Hudson, WI (US); Dennis J. Pohl, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 79 days.

(21) Appl. No.: 09/638,213

(22) Filed: Aug. 11, 2000

(51) Int. Cl.[7] ................................................ B32B 27/32

(52) U.S. Cl. ......................... 428/355 EN; 428/355 AC; 428/355 BL; 525/71; 525/80

(58) Field of Search .................. 428/355 EN, 355 AC, 428/355 BL; 525/71, 80

(56) References Cited

U.S. PATENT DOCUMENTS

| | | | |
|---|---|---|---|
| 4,181,752 A | 1/1980 | Martens et al. | |
| 4,619,979 A | 10/1986 | Kotnour et al. | |
| 4,737,559 A | 4/1988 | Kellen et al. | |
| 4,833,179 A | 5/1989 | Young et al. | |
| 4,843,134 A | 6/1989 | Kotnour et al. | |
| 5,637,646 A | 6/1997 | Ellis et al. | |
| 5,648,166 A | 7/1997 | Dunshee et al. | |
| 5,804,610 A | 9/1998 | Hamer et al. | |
| 5,876,855 A | 3/1999 | Wong et al. | |
| 5,891,957 A | 4/1999 | Hansen et al. | |
| 6,051,748 A | 4/2000 | Auguste et al. | 602/54 |

FOREIGN PATENT DOCUMENTS

| | | |
|---|---|---|
| EP | 0 554 832 | 8/1993 |
| EP | 0 699 727 | 3/1995 |
| WO | WO93/09713 | 5/1993 |
| WO | WO97/05171 | 2/1997 |
| WO | WO00/56828 | 3/1999 |

*Primary Examiner*—Robert Dawson
*Assistant Examiner*—Christopher M Keehan
(74) *Attorney, Agent, or Firm*—Carolyn V. Peters

(57) ABSTRACT

An adhesive blend is comprised of a hydrophilic pressure sensitive adhesive comprising the polymerization product of (a) about 15 to about 85 parts by weight of an (meth)acrylate ester monomer wherein the (meth)acrylate ester monomer, when polymerized, has a glass transition temperature ($T_g$) of less than about 10° C.; (b) about 85 to about 15 parts by weight of a hydrophilic acidic comonomer; and (c) at least about 10 parts based on 100 parts of the sum of components (a)+(b) of a non-reactive plasticizing agent and a hydrophobic pressure sensitive adhesive comprising an elastomer or thermoplastic elastomer including styrene block copolymers (e.g., linear, radial, tapered, star) consisting of copolymerized styrene and isoprene, butadiene or ethylene-butylene; polyisoprene; polybutadiene; polyisobutylene; butyl rubber; styrene-butadiepe rubber; natural rubber; and poly-α-olefins (e.g., polyhexene, polyoctene and propylene-hexene).

31 Claims, No Drawings

ADHESIVE BLENDS COMPRISING HYDROPHILIC AND HYDROPHOBIC PRESSURE SENSITIVE ADHESIVES

FIELD OF INVENTION

This invention relates to adhesive blends comprising a hydrophilic pressure sensitive adhesive and a hydrophobic pressure sensitive adhesive, more particularly to dry- and wet-surface adhesion, which may be present in different layers in a multilayer structure.

BACKGROUND OF THE INVENTION

Pressure-sensitive adhesive (PSA) tapes have been used for more than half a century for a variety of marking, holding, protecting, sealing and masking purposes. Pressure-sensitive adhesive tapes comprise a backing or substrate, and a pressure-sensitive adhesive. Pressure-sensitive adhesives require no activation other than finger pressure, exert a strong holding force and should be removable from a smooth surface without leaving a residue.

Adhering to skin presents challenges to adhesive manufacturers due to the inherent variability of the properties of skin. Adhesion to skin is dependent upon many factors. These factors include but are not limited to the environment in which the recipient is located. For instance, adhesion to skin will vary on the same person depending upon the humidity. If the same person were tested for skin adhesion using a given adhesive in different climates, different adhesion results would be obtained depending upon if the person were located in an arid versus in a humid environment.

Furthermore, skin varies from individual to individual. One person may have extremely dry skin whereas another person may have oily skin. As well as varying from individual to individual, skin properties may vary on a given individual depending upon the location on the body. For instance, skin located on a hand may be considerably drier than skin located on a back or face. Therefore, it is very difficult to manufacture a skin adhesive that is suitable for environmental and individual variabilities.

Adhesive composition and performance are also dependent upon the intended use of the adhesive. Use of PSAs for masking tape, or pavement markings will differ from uses for medical applications. While all applications require some wet-stick capabilities, there will be different requirements for the applications. For example, some uses require a gentle adhesive, such as adherence to a sensitive area whereas other uses require a more aggressive adhesive, such as when it is necessary that the adhesive remain adhered for an extended period of time or if the adhesive is adhered to an area which is very mobile.

Medical adhesives are generally used in wound dressings, surgical drapes, bandages and tapes. These items are generally constructed of a backing coated with an adhesive. The performance of the adhesive is in part dependent upon the occlusivity of the backing. Backings are generally categorized by their porosity into either nonocclusive or occlusive backings. When occlusive backings are used to prepare bandages or the like for medical applications the resulting bandage typically does not adhere well to skin over extended time periods. This probably occurs because the bandage cannot release water vapor that causes retention of moisture and in turn causes the adhesive to lift from the skin.

Conformability and cohesiveness are inversely related properties and are considered when preparing or selecting adhesives for end-uses, particularly for medical articles and medical applications. It is desirable for a medical adhesive to conform to the terrain of the skin to which it is adhered. This enhances comfort to the wearer and also ensures a higher initial adhesion to the skin because the adhesive is able to flow into the skin's topography. However, if an adhesive is too conformable it may lack the necessary cohesiveness necessary to remove the article with the adhesive intact. If an adhesive lacks cohesive strength the adhesive on a bandage may split upon an attempt to remove the article leaving some adhesive residue adhered to the skin and some adhesive removed along with the bandage backing. This is unacceptable to most medical professionals and patients.

Pressure-sensitive adhesives require a delicate balance of viscous and elastic properties that result in a four-fold balance of adhesion, cohesion, stretchiness and elasticity. Pressure-sensitive adhesives generally comprise a polymer that is either inherently tacky or can be tackified with the addition of tackifying resins. They can be coated in solvent or as water-based emulsions to reduce the material viscosity to a level that is easily applied to a substrate of choice.

Generally, when additives are used to enhance properties of pressure-sensitive adhesives they are required to be miscible with the pressure-sensitive adhesive or to have some common blocks or groups to permit homogeneous blends to form at the molecular level. Pressure-sensitive adhesives have been modified to extend their applicability into new areas. Tackified thermoplastic elastomers have been dissolved in acrylic monomers and subsequently cured. Tackified thermoplastic elastomers have also been added to polymerized acrylic pressure-sensitive adhesives in solvent where each component contains a common segment to permit compatibility. Natural rubber has been added to polymerized acrylic pressure-sensitive adhesives in solvent and subsequently thermally cured. The general purpose is to combine the high shear properties of elastomers with the high tack performance of acrylics to achieve adhesion to both polar and nonpolar surfaces. Further improvements and better balance of properties continue to be sought.

Pressure sensitive adhesives that adhere to wet or moist surfaces, so-called hydrophilic or "wet-stick" adhesives, are useful in many industrial, commercial and consumer applications. In pharmaceutical and other medical fields, such hydrophilic adhesives are typically used for adhering articles such as tapes, bandages, dressings, and drapes to moist skin surfaces such as wounds or areas of the body prone to moistness. Hydrophilic adhesives also find use in outdoor or exterior applications, such as on roadway materials, traffic control signage, and marine or automotive coatings and surfaces. Labels for food containers and other products that are exposed to moisture due to condensation or subjected to water or ice immersion also must be coated with hydrophilic adhesives.

(Meth)acrylate pressure sensitive adhesives are attractive materials for many tape and label applications because of their hydrophilic character. Copolymerization of (meth) acrylate monomers with hydrophilic acidic comonomers can increase hydrophilic characteristics and can enhance the cohesive strength of the PSA. However, this increased cohesive strength generally diminishes the tack of the hydrophilic acidic comonomer-containing (meth)acrylate copolymer.

At higher acidic comonomer levels, (meth)acrylate copolymers can dramatically lose their tack and become highly hydrophilic. When exposed to water, the moisture helps to transform these highly acidic, low tack compositions into tacky materials that are suitable as wet-stick adhesives used in many medical applications. When the water is allowed to evaporate, these adhesives lose their pressure-sensitive tack. Such compositions can also be useful as water-soluble or water dispersible adhesives. Water-dispersible or soluble (meth)acrylate copolymers can be formulated as repulpable adhesives used to splice dry paper rolls and designed to lose adhesive integrity and fully degrade when undergoing paper recycling operations.

When using high levels of acidic comonomers, it is difficult to effectively copolymerize these materials without a solvent, an aqueous reaction medium, or additives that promote interpolymerization of these monomers. Attempts to copolymerize these monomers in the absence of compatibilizing reaction media often results in heterogeneous materials dominated by glassy regions formed by the polymerization of the acidic comonomers and softer domains comprising the polymerized (meth)acrylate monomers. Thus, (meth)acrylate copolymers having high levels of acidic comonomers have traditionally been made using either solvent or water-based polymerization methods.

SUMMARY OF THE INVENTION

Briefly, in one aspect of the present invention an adhesive composition is provided comprising a blend of a hydrophilic pressure sensitive adhesive (PSA) (Component I) and a hydrophobic PSA (Component II). Suitable adhesive blend compositions of the present invention comprise a Component I to Component II weight ratio of from about 1:19 to about 19:1 (approximately 5/95 and 95/5 weight percent); preferable adhesive compositions comprise a Component I to Component II weight ratio of from about 1:9 to about 9:1 (approximately 10/90 and 90/10 weight percent); more preferable adhesive compositions comprise a Component I to Component II weight ratio of from about 1:4 to about 4:1 (approximately 20/80 and 80/20 weight percent); and most preferable adhesive compositions comprise a Component I to Component II weight ratio of from about 1:3 to about 3:1 (approximately 25/75 and 75/25 weight percent).

The present invention provides an adhesive composition comprising a blend of a hydrophilic PSA and a hydrophobic PSA, wherein the hydrophilic component comprises the polymerization product of (a) about 15 to about 85 parts by weight of an (meth)acrylate ester monomer wherein the (meth)acrylate ester monomer, when polymerized, has a glass transition temperature ($T_g$) of less than about 10° C.; (b) about 85 to about 15 parts by weight of a hydrophilic acidic comonomer; and (c) at least about 10 parts based on 100 parts of the sum of components (a)+(b) of a non-reactive plasticizing agent and wherein the hydrophobic component is an elastomer or thermoplastic elastomer including but not limited to styrene block copolymers (e.g., linear, radial, tapered, star) consisting of copolymerized styrene and isoprene, butadiene or ethylene-butylene; polyisoprene; polybutadiene; polyisobutylene; butyl rubber; styrene-butadiene rubber; natural rubber; and poly-α-olefins (e.g., polyhexene, polyoctene and propylene-hexene).

Inherently tacky elastomers and thermoplastic elastomers do not require the addition of a tackifying resin or plasticizer, although tackifying resins and plasticizers could be added to the elastomers or thermoplastic elastomer. On the other hand, tackifying resins and/or plasticizers are added to non-tacky elastomers and thermoplastic elastomers to provide the hydrophobic adhesive (Component II). Preferably, when used, tackifying resins and plasticizers are soluble in the elastomers or thermoplastic elastomers of Component II.

Potential additives that may be added to Component I, Component II, or to the blend of components I and II include initiators, chain transfer agents, pigments, fillers, medicinal additives, hollow or solid microspheres (expandable and non-expandable), as well as compatibilizing agents including block copolymers and homopolymers.

In another aspect, adhesive coated articles are provided, such as medical tapes, pavement marking tapes, labels, duct tapes, masking tapes, and other articles useful for dry- and wet-surfaces, such as wound dressings, and surgical drapes.

Advantageously, the blend of hydrophilic PSAs with hydrophobic PSAs provides for an improved balance of adhesion performance to both dry and wet surfaces, particularly for skin surfaces. Preferably, as measured by the Test Protocols described herein, the adhesive articles of the present invention have an initial ($T_0$) adhesion to wet skin and to dry skin of at least about 0.8 N/dm and no greater than about 8.0 N/dm; and have an extended (24 to 48 hours, $T_{24-48}$) of no greater than about 15 N/dm. Further, the adhesive compositions of the present invention may also have an initial peel adhesive (bond between the adhesive layer and the testing surface) to stainless steel underwater that is at least 16 N/dm, while the two-bond (bond between the adhesive layer and the substrate) is at least 25 N/dm.

In another aspect of the present invention, a method of using the adhesive blends of the present invention is provided comprising the steps of: (a) applying a layer of the adhesive blend to a predetermined thickness onto a substrate, and (b) applying. the layered substrate onto a wet or dry surface. Further, the wet or dry surface is wet or dry skin.

In yet another aspect of the present invention, a pressure sensitive adhesive article is provided comprising a substrate and a pressure sensitive adhesive composition disposed thereon, wherein the pressure sensitive adhesive composition comprises a blend of (I) a hydrophilic pressure sensitive adhesive and (II) a hydrophobic pressure sensitive adhesive, wherein the substrate is selected from the group of cloth, metallized foil, metallized film, polymeric film, nonwoven polymeric material, paper, foam, and combinations thereof As used herein in this application:

"pressure-sensitive adhesive" or "PSA" refers to a viscoelastic material that possesses the following properties: (1) aggressive and permanent tack, (2) adherence with no more than finger pressure, (3) sufficient ability to hold onto a substrate, and (4) sufficient cohesive strength to be removed cleanly from the substrate;

"hydrophilic adhesive" refers to a material that exhibits pressure-sensitive adhesive properties when adhered to a wet substrate. Hydrophilic adhesives may or may not demonstrate pressure-sensitive adhesive properties under dry conditions;

"(meth)acrylate monomers" are acrylic acid esters or methacrylic acid esters of non-tertiary alcohols, the alcohols preferably having about 4 to 12 carbon atoms;

"hydrophilic acidic comonomers" are water soluble ethylenically unsaturated, free radically reactive monomers having carboxylic, sulfonic or phosphonic acid functionality and are copolymerizable with the (meth)acrylate monomers;

"compatible" when referring to plasticizing agents (as used in Component I) means plasticizing agents that:

1) exhibit no gross phase separation from the hydrophilic adhesive when present in the prescribed amounts,
2) once mixed with the hydrophilic adhesive, do not significantly phase separate from the hydrophilic adhesive upon aging, 3) function as a rheological modification agent for the hydrophilic adhesive, such that this plasticized adhesive exhibits pressure-sensitive properties as defined above, and 4) promote high conversion polymerization, that is greater than 98% polymerization of the comonomers;

"non-reactive" refers to plasticizing agents that do not contain free radically reactive ethylenically unsaturated groups that could co-react with the comonomers or functionalities that significantly inhibit the polymerization of these monomers;

"non-volatile" refers to plasticizing agents that, when present in the hydrophilic adhesive, generate less than 3% VOC (volatile organic content). The VOC content can be determined analogously to ASTM D 5403-93 by exposing the coated hydrophilic adhesive to 100°±5° C. in a forced draft oven for 1 hour. If less than 3% plasticizing agent is lost from the plasticized pressure-sensitive adhesive, then the plasticizing agent is considered "non-volatile";

"solventless" refers to hydrophilic adhesive polymerizable mixtures that are essentially 100% solid systems. Usually, such polymerizable mixtures have no more than about 5% organic solvents or water, more typically no more than about 3% organic solvents or water. Most typically, such polymerizable mixtures are free of organic solvents and water.

DESCRIPTION OF THE PREFERRED EMBODIMENT(S)

Adhesives blends of the present invention uniquely balance dry- and wet-surface adhesion characteristics and comprise a hydrophilic PSA (Component I) and a hydrophobic PSA (Component II). The adhesive blends can optionally include additives.

Component I-Hydrophilic Pressure Sensitive Adhesive

Component I comprises a hydrophilic wet-stick polyacrylate PSA comprising the polymerization product of: at least one (meth)acrylate monomer, at least one hydrophilic acidic comonomer, and at least one plasticizing agent. Furthermore, the polymerizable mixture typically contains additional additives, including initiators, chain transfer agents, and/or other additives, such as pigments, glass or polymeric bubbles or beads (which may be expanded or unexpanded), fibers, reinforcing agents, hydrophobic or hydrophilic silica, toughening agents, fire retardants, antioxidants, finely ground polymeric particles such as polyester, nylon, and polypropylene, and stabilizers.

(Meth)acrylate Monomer

The hydrophilic PSAs used as a component of the adhesive blends of the present invention contain at least one monofunctional unsaturated monomer selected from the group consisting of (meth)acrylate esters of non-tertiary alkyl alcohols, the alkyl groups of which preferably comprise from about 4 to about 12 carbon atoms, more preferably about 4 to about 8 carbon atoms; and mixtures thereof. Preferred (meth)acrylate monomers have the following general Formula (I):

Formula (I)

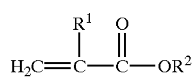

wherein $R^1$ is H or $CH_3$. $R^2$ is selected from linear or branched hydrocarbon groups and may contain one or more heteroatoms. The number of carbon atoms in the hydrocarbon group is preferably about 4 to about 12, and more preferably about 4 to about 8.

Examples of suitable (meth)acrylate monomers useful in the present invention include, but are not limited to, n-butyl acrylate, decyl acrylate, 2-ethylhexyl acrylate, hexyl acrylate, isoamyl acrylate, isodecyl acrylate, isononyl acrylate, isooctyl acrylate, lauryl acrylate, 2-methyl butyl acrylate, 4-methyl-2-pentyl acrylate, ethoxy ethoxyethyl acrylate and mixtures thereof. Particularly preferred are n-butyl acrylate, 2-ethylhexyl acrylate, isooctyl acrylate, lauryl acrylate, and mixtures thereof Hydrophilic Acidic Comonomer Useful hydrophilic acidic comonomers include, but are not limited to, those selected from ethylenically unsaturated carboxylic acids, ethylenically unsaturated sulfonic acids, ethylenically unsaturated phosphonic acids, and mixtures thereof. Examples of such comonomers include those selected from acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like, and mixtures thereof. Particularly preferred hydrophilic acidic monomers are ethylenically unsaturated carboxylic acids, most preferably, acrylic acid.

Minor amounts (e.g., not greater than about 10% by weight) of monomers copolymerizable with both the (meth) acrylate monomers and hydrophilic acidic monomers can be used. Examples of such monomers include (meth) acrylamides, vinyl esters and N-vinyl lactams.

The copolymerizable mixture used to make the hydrophilic adhesive comprises, based upon 100 parts by weight total, about 15 to about 85 parts by weight of at least one (meth)acrylate monomer and about 85 to about 15 parts by weight of a hydrophilic acidic comonomer. Preferably, the copolymerizable mixture comprises about 20 to about 80 parts by weight of at least one (meth)acrylate monomer and about 80 to about 20 parts by weight of a hydrophilic acidic comonomer. More preferably, the copolymerizable mixture comprises about 40 to about 60 parts by weight of at least one (meth)acrylate monomer and about 60 to about 40 parts by weight of a hydrophilic acidic comonomer. The ratio of each comonomer in the hydrophilic adhesive can be chosen to optimize the performance.

Plasticizing Agent

Useful plasticizing agents are compatible with the starting monomers and the resultant polymers of the hydrophilic pressure sensitive adhesive, such that once the plasticizing agent is mixed with the monomers or the resulting polymers, the plasticizing agent does not phase separate. By "phase separation" or "phase separate", it is meant that by differential scanning calorimetry (DSC) no detectable thermal transition, such as a melting or glass transition temperature, can be found for the pure plasticizing agent in the wet stick adhesive composition.

Preferably, the plasticizing agent is non-volatile and non-reactive. Particularly useful plasticizing agents include polyalkylene oxides having weight average molecular weights of about 150 to about 5,000, preferably of about 150 to about 1,500, such as polyethylene oxides, polypropylene oxides, polyethylene glycols, and copolymers thereof; alkyl or aryl functionalized polyalkylene oxides, such as PYCAL 94 (a phenyl ether of polyethylene oxide, commercially available from ICI Chemicals); benzoyl functionalized polyethers, such as Benzoflex 400 (polypropylene glycol dibenzoate, commercially available from Velsicol Chemicals) and monomethyl ethers of polyethylene oxides, and mixtures thereof. Examples of other useful plasticizing agents include CARBOWAX™ MPEG 550, a methoxypolyethylene glycol plasticizer having a molecular weight of approximately 550 and available from Union Carbide Corp.; Polyol PPG 1025, a polypropylene glycol plasticizer having a molecular weight of approximately 1025 and available from Lyondell Chemical Worldwide, Inc.; Polyol PPG 425, a polypropylene glycol plasticizer having a molecular weight of approximately 425 and available from Lyondell Chemical Worldwide, Inc.; and PLURONIC™ 25R4, an ethylene oxide/propylene oxide block copolymer plasticizer available from BASF Company.

The plasticizing agent can be used in amounts of at least about 10 pph (parts by weight per 100 parts of the (meth) acrylate monomers and hydrophilic acidic comonomers). Typically, the plasticizing agent is present in the adhesive in amounts from about 15 to 100 pph. Preferably, the plasticizing agent is present in amounts from about 20 to 80 pph. The amount of plasticizer required depends upon the type and ratios of the (meth)acrylate monomers and hydrophilic acidic comonomers employed in the polymerizable mixture and the chemical class and molecular weight of the plasticizing agent.

Additives

A. Initiators

A free radical initiator is preferably added to aid in the copolymerization (meth)acrylate comonomers and acidic comonomers. The type of initiator used depends on the polymerization process. Photoinitiators which are useful for polymerizing the polymerizable mixture monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1,1-propanedione-2-(o-ethoxycarbonyl) oxime. Examples of commercially available photoinitiators are IRGACURE™ 651 (2,2-dimethoxy -1,2-diphenylethane-1-one) and IRGACURE™ 184 (a hydroxycyclohexyl phenyl ketone), both commercially available from Ciba-Geigy Corporation. Generally, the photoinitiator is present in an amount of about 0.005 to 1 weight percent based on the weight of the copolymerizable monomers. Examples of suitable thermal initiators include AIBN (2,2'-azobis(isobutyronitrile), hydroperoxides, such as tert-butyl hydroperoxide, and peroxides, such as benzoyl peroxide and cyclohexane peroxide. Depending on the particular initiator used, the product resulting from the copolymerization reaction may further comprise a residue of the polymerization initiator.

B. Chain Transfer Agents

Preferably, the polymerizable mixture also includes a chain transfer agent to control the molecular weight of the polymerized compositions. Chain transfer agents are materials that regulate free radical polymerization and are generally known in the art. Suitable chain transfer agents include halogenated hydrocarbons such as carbon tetrabromide; sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether and mixtures thereof The amount of chain transfer agent that is useful depends upon the desired molecular weight and the type of chain transfer agent. The chain transfer agent is typically used in amounts from about 0.001 part to about 10 parts by weight per 100 parts of total monomer, and preferably from about 0.01 part to about 0.5 part, and most preferably from about 0.02 part to about 0.20 part.

C. Other Additives

Other additives can be included in the polymerizable mixture to change the properties of the adhesive. Such additives include fillers, pigments, chemical or physical blowing agents, anti-microbials, antibiotics, medicinal additives, glass or polymeric bubbles or beads (which may be expanded or unexpanded), fibers, reinforcing agents, hydrophobic or hydrophilic silica, toughening agents, fire retardants, antioxidants, finely ground polymeric particles such as polyester, nylon, and polypropylene, and stabilizers. Crosslinking agents could also be added, such as copolymerizable mono-ethylenically unsaturated aromatic ketone comonomers free of ortho-aromatic hydroxyl groups such as those disclosed in U.S. Pat. No. 4,737,559. Specific examples of useful crosslinking agents include para-acryloxybenzophenone, para-acryloxyethoxybenzophenone, para-N-(methylacryloxyethyl)-carbamoylethoxybenzophenone, para-acryloxyacetophenone, ortho-acrylamidoacetophenone, acrylated anthraquinones, and the like. A preferred crosslinking agent is acryloyloxybenzophenone. When used, additives are added in amounts sufficient to affect the desired end properties, as known to those skilled in the art.

Methods

A method for preparing a hydrophilic pressure sensitive adhesive comprises the steps of:

(a) combining a polymerizable mixture comprising:
  (i) about 15 to about 85 parts by weight of an (meth) acrylate ester monomer wherein the (meth)acrylate ester monomer, when homopolymerized, has a Tg of less than about 10° C.;
  (ii) about 85 to about 15 parts by weight of a hydrophilic acidic comonomer; and
  (iii) at least about 10 parts based on 100 parts of the sum of components (a)+(b) of a non-reactive plasticizing agent; and
(b) polymerizing the polymerizable mixture to form a pressure sensitive adhesive that adheres to wet substrate surfaces.

An alternative method for preparing a hydrophilic pressure sensitive adhesive comprises the steps of:

(a) combining a polymerizable mixture comprising:
  (i) about 15 to about 85 parts by weight of an (meth) acrylate ester monomer wherein the (meth)acrylate ester monomer, when homopolymerized, has a Tg of less than about 10° C.;
  (ii) about 85 to about 15 parts by weight of a hydrophilic acidic comonomer; and
  (iii) at least about 10 parts based on 100 parts (a)+(b) of a non-reactive plasticizing agent;
(b) enveloping the polymerizable mixture in a packaging material; and
(c) exposing the enveloped polymerizable mixture to radiation sufficient to polymerize the polymerizable mixture and to form a pressure sensitive adhesive that adheres to wet substrate surfaces.

Yet another method for preparing a hydrophilic pressure sensitive adhesive comprises the steps of:

(a) preparing a prepolymeric syrup comprising:
  (i) about 15 to about 85 parts by weight of an (meth) acrylate ester monomer wherein the (meth)acrylate ester monomer, when homopolymerized, has a Tg of less than about 10° C.; and (ii) about 85 to about 15 parts by weight of a hydrophilic acidic comonomer;

(b) combining the prepolymeric syrup with at least about 10 parts based on 100 parts of the sum of components (i)+(ii) of a non-reactive plasticizing agent to form a polymerizable mixture; and (c) exposing the polymerizable mixture to radiation sufficient to polymerize the polymerizable mixture and to form a pressure sensitive adhesive that adheres to wet substrate surfaces.

Polymerization Processes

Polymerization methods, such as the continuous free radical polymerization method described in U.S. Pat. Nos. 4,619,979 and 4,843,134; the essentially adiabatic polymerization methods using a batch reactor described in U.S. Pat. No. 5,637,646; and, the methods described for polymerizing packaged polymerizable mixtures described in U.S. Pat. No. 5,804,610 may be utilized to prepare the polymers.

Polymerization can also be effected by exposure to ultraviolet (UV) radiation as described in U.S. Pat. No. 4,181, 752.

Component II-Hydrophobic Pressure Sensitive Adhesive

Component II comprises a hydrophobic PSA that includes an elastomer or thermoplastic elastomer and, optionally, a tackifying resin and/or plasticizer.

Thermoplastic Elastomer

Thermoplastic elastomeric materials are generally defined as materials that behave as elastomers at ambient temperatures, but are thermoplastic at elevated temperatures where they can be molded and remolded. Thermoplastic elastomeric materials useful in the present invention include, for example, linear, radial, star and tapered styrene-isoprene block copolymers such as Kraton™ D 1107 and Kraton™ D1113, both available from Shell Chemical Co., Houston, Tex.; EUROPRENE™ SOL TE 9110, available from EniChem Elastomers Americas, Inc., Houston, Tex.; linear styrene-(ethylene-butylene) block copolymers such as Kraton™ G1657, available from Shell Chemical Co.; linear styrene-(ethylene-propylene) block copolymers such as Kraton™ G1701, available from Shell Chemical Co.; linear, radial, and star styrene-butadiene block copolymers such as Kraton™ D 1118X, available from Shell Chemical Co.; EUROPRENE™ SOL TE 6205, available from EniChem Elastomers Americas, Inc.; polyetheresters, such as HYTREL™ G3548, available from DuPont; poly-alpha-olefin-based thermoplastic elastomeric materials such as those represented by the formula —$(CH_2$—CHR)—, where R is an alkyl group containing 2 to 10 carbon atoms; and poly-alpha-olefins based on metallocene catalysis, such as ENGAGE™ EG8200, an ethylene/poly-alpha-olefin copolymer available from Dow Plastics Co., Midland, Mich.

B. Elastomer

Elastomeric materials are materials that generally form one phase at 21° C., have a glass transition temperature less than about 0° C., and exhibit elastic properties. Elastomers are among the group of polymers that can easily undergo very large, reversible elongations (up to 500 to 1000%) at relatively low stresses. Elastomeric materials useful in the present invention include, for example, natural rubbers such as CV-60, a controlled viscosity grade, and SMR-5, a ribbed smoked sheet rubber; butyl rubbers, such as Exxon Butyl 268 available from Exxon Chemical Co.; synthetic polyisoprenes such as Kraton™ IR305, available from Shell Chemical Co.; NATSYN™ 2210, available from Goodyear Tire and Rubber Co.; ethylene-propylenes; polybutadienes; polyisobutylenes, such as VISTANEX™ MM L-80, available from Exxon Chemical Co.; and styrene-butadiene random copolymer rubbers such as AMERIPOL™ 1011A, available from B F Goodrich, Akron, Ohio.

C. Tackifying Resin or Plasticizer

Optionally, these thermoplastic elastomeric or elastomeric materials can be modified with tackifying resins or plasticizers.

The tackifying resins or plasticizers may or may not be miscible with Component I. A tackifying resin or plasticizer, when present generally comprises about 5 to 300 parts by weight, more typically up to about 200 parts by weight, based on 100 parts by weight of the elastomer or the thermoplastic elastomer. Useful examples of tackifying resins suitable for the invention include but are not limited to liquid rubbers, aliphatic and aromatic hydrocarbon resins, rosin, natural resins such as dimerized or hydrogenated balsams and esterified abietic acids, polyterpenes, terpene phenolics, phenol-formaldehyde resins, and rosin esters. Preferred tackifying resins include Escorez™ 1310LC available from Exxon Chemical Co. and Wingtack™ 95 available from Goodyear Tire and Rubber Co. Useful examples of plasticizers include but are not limited to polybutene, paraffinic oils, naphthenic oils, petrolatum, and certain phthalates with long aliphatic side chains such as ditridecyl phthalate.

Additives

Additives such as pigments, fillers, medicinals (e.g., antimicrobials and other biologically active agents), crosslinkers, and antioxidants may be used in the adhesive blends of the present invention. Examples of fillers include but are not limited to inorganic fillers such as zinc oxide, alumina trihydrate, talc, titanium dioxide, aluminum oxide and silica. Other additives such as amorphous polypropylene or various waxes may also be used. Pigments and fillers may be incorporated into the adhesive blend in order to manipulate the properties of the adhesive according to its intended use. Radiation crosslinkers such as benzophenone, derivatives of benzophenone, and substituted benzophenones may be added to the adhesive blends of the invention. Finally, antioxidants may be used to protect against severe environmental aging caused by ultraviolet light or heat. Antioxidants include, for example, hindered phenols, amines, and sulfur and phosphorous hydroxide decomposers. A preferred antioxidant is IRGANOX™ 1010 available from Ciba-Geigy Corp.

Method of Making the Adhesive Blends

Although Components I and II are preferably blended and coated using melt extrusion techniques or by solvent coating, blending can be done by any method that results in a substantially homogeneous distribution of Components I and II.

If a hot melt coating is desired, a blend is prepared by melt mixing the components in the molten or softened state using devices that provide dispersive mixing, distributive mixing, or a combination of dispersive and distributive mixing. Both batch and continuous methods of blending may be used. Examples of batch methods include Brabender™ or Banbury™ internal mixing, and roll milling. Examples of continuous methods include single screw extruding, twin screw extruding, disk extruding, reciprocating single screw extruding, and pin barrel single screw extruding. The continuous methods can include both distributive elements such as cavity transfer elements such as CTM™, available from RAPRA Technology, Ltd., Shrewsbury, England, pin mixing elements, and static mixing elements and dispersive elements such as Maddock mixing elements or Saxton mixing elements.

An example of a batch process is the placement of a portion of the blend between the desired substrate to be coated and a release liner, pressing this composite structure in a heated platen press with sufficient temperature and pressure to form a pressure-sensitive coating of the desired thickness and cooling the resulting coating.

Continuous forming methods include drawing the pressure-sensitive adhesive composition out of a film die and subsequently contacting a moving plastic web or other suitable substrate. A related continuous method involves extruding the pressure-sensitive adhesive composition and a coextruded backing material from a film die and subsequently cooling to form a pressure-sensitive adhesive tape.

Other continuous forming methods involve directly contacting the pressure-sensitive adhesive blend to a rapidly moving plastic web or other suitable substrate. In this method, the pressure-sensitive adhesive blend can be applied to the moving web using a die having flexible die lips such as a reverse orifice-coating die. After forming, the pressure-sensitive adhesive coatings are solidified by quenching using both direct methods, such as chill rolls or water baths, and indirect methods, such as air or gas impingement.

Optionally, Components I and II are blended and coated using solvent blending and solvent coating techniques. However, it is preferable that Components I and II be substantially soluble in the solvents used. Mixing can be done by any method that results in a substantially homogeneous distribution of Component I and Component II.

Laminate Constructions-Substrates

The adhesive blends of the present invention are useful to prepare adhesive coated articles. The present invention provides adhesives that are skin-compatible and thus are particularly suitable for medical applications, such as surgical tapes and drapes, bandages, athletic tapes, wound dressings and the like. The adhesive blends may be coated onto any backing suitable for medical applications including occlusive (substantially non-breathable) and non-occlusive backings (breathable). Occlusive backings are also known as low porosity backings. Nonlimiting examples of occlusive backings include films, foams and laminates thereof Nonlimiting examples of non-occlusive backings include woven substrates, knit substrates, nonwoven substrates such as hydroentangled materials or melt blown webs, foams and thermally embossed nonwoven substrates.

The coated adhesive blends of the present invention can be crosslinked by exposure to ultraviolet radiation from, for example, medium pressure mercury arc lamps, or by exposure to an electron beam (e-beam). For example, coated adhesive blends can be irradiated with E-beam radiation at a level of 2 Mrad dosage at 175 kV directly after and in-line with the coating process using an ELECTOCURTAIN™ CB-175 electron beam system available from Energy Sciences, Inc., Wilmington, Mass..

This invention is further illustrated by the following examples that are not intended to limit the scope of the invention. In the examples, all parts, ratios and percentages are by weight unless otherwise indicated. The following test methods were used to evaluate and characterize the adhesive compositions and blends produced in the examples. All materials are commercially available, for example from Aldrich Chemicals, unless otherwise indicated or described.

EXAMPLES

Test Protocols

Adhesion to Steel

Adhesion to steel was determined without any sample dwell on the steel according to this procedure. Tape samples were cut into 2.5-cm by 30.5-cm strips. The samples were adhered to the center of a cleaned steel surface (cleaned with 50% n-heptane/50% isopropyl alcohol) adhesive side down, so that 12.7 to 17.8 cm of sample extended beyond the steel surface. The tape was rolled once in each direction with a 2.0-kg roller at a rate approximately 5.1 cm per second. The free end of the sample was then doubled back on itself and approximately 2.5 cm was peeled from the steel plate. The end of the panel from which the sample had been removed was placed in the lower jaw of an Instron tester. The free end was folded to form a small tab and was placed in the upper jaw as above. The sample was mechanically removed from the plate by activating the Instron at a crosshead speed of 30.5 cm per minute and data were recorded. The average of three peel values were reported in units of Newtons/decimeter (N/dm).

Adhesion to Dry and Wet Skin

Initial skin adhesion ($T_0$) and adhesion after varying dwell times ($T_{24}$, $T_{48}$) was measured by applying tape samples to wet and dry skin of human subjects. For dry skin adhesion testing, two samples (one for $T_0$ and one for $T_{24}$ or $T_{48}$), each measuring 2.5-cm wide by 7.6-cm long, were applied to the back of each of six human subjects. The subjects were placed in a prone position with arms at their sides and heads turned to one side. Samples were applied without tension or pulling of skin to both sides of the spinal column with the length of each sample positioned at a right angle to the spinal column.

For initial ($T_0$) wet skin adhesion testing, samples were applied in the manner described above to skin which had been sprayed with a measured amount of water (about 20 microliters), so that the skin was visibly wet, immediately before application of the sample.

The samples were pressed into place with a 2-kg roller moved at a rate of approximately 2.5 cm/sec with a single forward and reverse pass. No manual pressure was applied to the roller during application.

The samples were then removed five minutes ($T_0$ wet or dry), or 24 or 48 +/−2 hours ($T_{24}$/$T_{48}$) after application at a removal angle of 180° and at a removal rate of 15 cm/min using a conventional adhesion tester equipped with a 11.3-kg test line attached to a 2.5-cm clip. The clip was attached to the edge of the sample furthest from the spinal column by manually lifting about 1 cm of the sample from the skin and attaching the clip to the raised edge. The adhesion tester was a strain gauge mounted on a motor-driven carriage.

The measured force required to effect removal of each tape sample was reported (as an average of 6 sample replications) in Newtons per dm. Preferably, initial adhesion to wet or dry skin is at least 0.8 N/dm and no greater than 8.0 N/dm. Extended (i.e., 24 to 48 hours) adhesion is preferably no greater than 15 N/dm.

Porosity

Porosity was evaluated by a procedure wherein the time (in seconds) necessary for an inner cylinder of a Gurley densometer to force 100 cc of air through a 25-mm circular sample of the sample is determined in a manner analogous to that described in ASTM D737-75. Samples with Gurley porosity values of >100 sec are considered occlusive.

Moisture Vapor Transmission Rate (MVTR)

MVTR was evaluated in a manner analogous to that described in ASTM E 96-80 at 40° C. and expressed in grams transmitted per square meter per day ($g/m^2/24$ hr). A tape sample must exhibit an MVTR value of not less than 500 $g/m^2/24$ hr to be considered permeable to water vapor.

Two-Bond Adhesion

The two-bond adhesion method was used to measure the force necessary to remove a pressure sensitive adhesive coating from its backing. Specimens were cut into 2.5-cm wide×20-cm long strips. Using a clean steel plate, a 5-cm wide strip of double-coated adhesive tape (3M Brand Double Stick Tape, 3M Co., St. Paul, Minn.) with liner removed was centered and attached to the plate. With its adhesive side face-up, a tape specimen was applied to the double-coated tape. A 24-cm long×1.27-cm wide strip of a test tape (Scotch™ No. 56 Electrical Tape, 3M Co.) was then centered and applied adhesive side down onto the tape specimen. The construction was then rolled down by 1 pass of a 2.0-kg roller at a rate of 230 cm/min. The remaining length of the test tape (approximately 4 cm) was then secured to a stationary load cell such that with the movement of the carriage, a 180° peel angle would be attained. The carriage moved at a rate of 230 cm/min. The force required to remove the adhesive from the tape specimen was reported in Newtons/decimeter (average of 2 replicas) and observations of any tape adhesion failures were noted.

Peel Adhesion to Glass (21° C. and 4° C.) and Stainless Steel (21° C.)

The peel adhesion method was used to measure the force required to remove an adhesive-coated sample from a test substrate surface at a specific angle and rate of removal. The room temperature peel adhesion was measured at 21° C. and 50% RH against either a clean glass or stainless steel plate. A tape sample (1.25-cm wide×15-cm long) was adhered to the test substrate using one pass of 2.1-kg rubber-faced roller and tested using a Model 3M90 Slip/Peel tester (IMASS, Inc., Accord, Mass.) at an angle of 180° and a rate of 229 cm/min. For 4° C. peel adhesion to glass, tape samples were conditioned at 4° C. for 24 hours before testing. Two replicas were run and an average result was recorded in N/dm.

Shear to Stainless Steel (SS)

Shear strength, as determined by holding time, was measured for adhesive-coated tape samples against a clean stainless steel substrate. A tape sample (12.5-cm wide×25-cm long) was conditioned for greater than 24 hours at approximately 21° C. and 50% RH and adhered to the steel substrate surface using four passes of a 2.1-kg rubber-faced roller. The taped substrate was placed in a vertical holding rack, a static 500-gram load was attached to the tape at an angle of 180°, and the time for the load to drop was measured in minutes. For those samples still adhering to the substrate after 4000 minutes, the test was discontinued. Two replicas were run and an average result was recorded in minutes.

Under-Water Adhesion to SS (1.0-Minute and 960-Minute Dwell Times)

The under-water peel adhesion method was used to measure the force required to remove an adhesive-coated sample from an under-water test substrate surface at a specific angle and rate of removal. A tape sample (1.25-cm wide×15-cm long) was conditioned for greater than 24 hours at approximately 21° C. and 50% relative humidity. The adhesive side of the sample was immersed in water for 1.0 minute and then rolled down using one pass of a 2.1-kg rubber-faced roller on a clean stainless steel (SS) plate under about a 2.5-cm thick layer of water. After a defined under-water dwell time of 1.0 or 960 minutes, the tape sample was tested using a Model 3M90 Slip/Peel tester (from IMASS, Inc.) at an angle of 180° and at a peel rate of 229 cm/min at a temperature of approximately 21° C. and 50% RH. Two replicas were run at each dwell time and the average results were recorded in N/dm.

| Glossary | |
|---|---|
| 2EHA | 2-ethylhexyl acrylate |
| AA | acrylic acid |
| IOA | isooctyl acrylate |
| MPEG 550 | CARBOWAX MPEG 550 is a methoxypolyethylene glycol plasticizer having a molecular weight of approximately 550 (commercially available from Union Carbide Corp., Tarrytown, NY) |
| PPG 1025 | Polyol PPG 1025 is a polypropylene glycol plasticizer having a molecular weight of approximately 1025 (commercially available from Lyondell Chemical Worldwide, Inc., Houston, TX) |
| PPG 425 | Polyol PPG 425 is a polypropylene glycol plasticizer having a molecular weight of approximately 425 (commercially available from Lyondell Chemical Worldwide, Inc.) |
| 25R4 | PLURONIC ™ 25R4 is an ethylene oxide/propylene oxide block copolymer plasticizer (commercially available from BASF Company, Parsippany, NJ) |
| PYCAL ™ 94 | a polyethylene oxide phenyl ether plasticizer (commercially available from ICI Chemicals, Inc., Wilmington, DE) |
| Kraton ™ D1107 | a styrene-isoprene copolymer thermoplastic elastomer containing 14 wt. % polystyrene and 86 wt. % polyisoprene (commercially available from Shell Chemical Co., Houston, TX) |
| Kraton ∩ D1113 | a styrene-isoprene copolymer thermoplastic elastomer containing 16 wt. % polystyrene and 84 wt. % polyisoprene (commercially available from Shell Chemical Co.) |
| NATSYN ™ 2210 | a synthetic polyisoprene rubber (commercially available from Goodyear Tire and Rubber Co., Akron, OH) |
| IR305 | Kraton ™ IR305, a synthetic polyisoprene rubber (commercially available from Shell Chemical Co.) |
| Elastomer A | Styrene/isoprene block copolymer having a styrene content of 9.4% by weight as described for Polymer B in Table 2 of U.S. Pat. No. 5,296,547 (Nestegard et al.) |
| Escorez ™ 1310 LC | a tackifier aliphatic resin (commercially available from Exxon Chemical Co., Houston, TX)Wingtack ™ 95 a tackifier of a synthetic polyterpene resin (commercially available from Goodyear Tire and Rubber Co., Akron, OH) |
| COMP A | PS-PVPy (5%) compatabilizer made of poly(styrene-co-vinylpyridine) with 5% vinylpyridine (PVPy) block was made similar to the procedure described for Compatibilizer B in U.S. patent application Ser. No. 09/499,831 (Cernohous, et al), except in zone 4, purified 4-vinylpyridine was added (at a rate of 7.5 g/min instead of 15.0 g/min) |
| COMP B | PS-PVPy (30%) compatabilizer made of poly(styrene-co-vinylpyridine) with 30% vinylpyridine (PVPy) block was made similar to the procedure described for Compatibilizer B in U.S. patent application Ser. No. 09/499,831 (Cernohous, et al), except in zone 4, purified 4-vinylpyridine was added (at a rate of 45.0 g/min instead of 15.0 g/min) |
| IRGANOX ™ 1010 | an antioxidant, tetrakis[methylene-3-(3',5'-di-tert-butyl-4'-hydroxyphenyl)propionate]methane (commercially available from Ciba-Geigy Corp., Switzerland) |
| IRG 184 | IRGACURE ™ 184, a hydroxycyclohexyl phenyl ketone photoinitiator (commercially available from Ciba-Geigy Corp., Switzerland) |
| IRG 651 | IRGACURE ™ 651 (2,2-dimethoxy-1,2-diphenylethane-1-one) photoinitiator (commercially available from Ciba-Geigy Corp., Switzerland) |
| IOTG | a chain transfer agent, isooctyl thioglycolate (commercially available from Hampshire Chemical, a subsidiary of the Dow Chemical Company, Lexington, MA) |

Hydroplilic Adhesive Starting Materials

The compositions of the hydrophilic, wet-stick, polyacrylate adhesives (PAA) used to prepare the adhesive blends of the invention are provided in Table 1. Adhesives PAA-1 to PAA-11 were prepared by a solventless polymerization process and packaged in acrylic pouches as described in Examples 1–13 of U.S. patent application Ser. No. 09/367,455. The UV exposure time was 9 minutes.

A traditional, nonhydrophilic, non wet-stick, polyacrylate PSA (CA-1) was used to prepare an adhesive blend as a comparative example. CA-1 is an IOA/methacrylic acid (MAA) 96/4 copolymer PSA, prepared as described in US Pat. No. 4,833,179 (Young et al).

TABLE 1

Hydrophilic Polyacrylate Adhesives (PAA)

| Adhesive No. | Acrylate | Parts | AA (Parts) | Plasticizer | Parts | IOTG (Parts) | IRG 184 (Parts) |
|---|---|---|---|---|---|---|---|
| PAA-1 | IOA | 38 | 28 | MPEG 550 | 34 | 0.07 | 0.15 |
| PAA-2 | IOA | 35 | 30 | MPEG 550 | 35 | 0.07 | 0.15 |
| PAA-3 | IOA | 37 | 31.5 | MPEG 550 | 31.5 | 0.07 | 0.15 |
| PAA-4 | IOA | 34 | 33 | MPEG 550 | 33 | 0.07 | 0.15 |
| PAA-5 | IOA | 36 | 31 | MPEG 550 | 33 | 0.07 | 0.25 |
| PAA-6 | 2EHA | 30 | 30 | MPEG 550 | 40 | 0.03 | 0.50 |
| PAA-7 | 2EHA | 25 | 25 | PPG 1025 | 50 | 0.03 | 0.50 |
| PAA-8 | 2EHA | 25 | 25 | PPG 425 | 50 | 0.03 | 0.50 |
| PAA-9 | 2EHA | 65 | 15 | 25R4 | 20 | 0.05 | 0.50 |
| PAA-10 | 2EHA | 29.4 | 29.4 | PYCAL 94 | 41.2 | 0.03 | 0.15* |
| PAA-11 | 2EHA | 30.3 | 30.3 | PYCAL 94 | 39.4 | 0.03 | 0.15* |

*IRG 651 was used in place of IRG 184 for Adhesive Nos. PAA-10 and PAA-11

EXAMPLES 1–27 and

Comparative Examples 1–9

Adhesive Blends Prepared by Hot Melt Process

The adhesive blends of Examples 1–27 were prepared by combining together hydrophilic PAA, elastomer, and tackifier components according to the following procedure. The acrylic pouches of PAA were melted, masticated, and fed into barrel 7 of a fully intermeshing and co-rotating twin screw extruder (TSE) (Model ZSK 30, available from Werner & Pfleiderer, Ramsey, N.J., having a 30-mm diameter, 36 to 1 length to diameter and 12 barrel sections) using a 5.08-cm Bonnot extruder (available from the Bonnot Company, Uniontown, Ohio). The Bonnot temperatures were controlled between 76–93° C. and fitted with a metering Zenith gear pump (available from Zenith Products Company, West Newton, Mass.). The elastomer component (e.g., Kraton™ D1107 or pre-pelletized Natsyn™ 2210) was dry-fed using a K-TRON™ gravimetric feeder (available from K-TRON™ International, Incorporated, Pitman, N.J.) into an open port of barrel 1 of the TSE. The tackifying resin component (e.g., Escorez™ 1310 or Wingtack™ 95) was optionally dry-blended with an antioxidant (e.g., IRGANOX™ 1010). The tackifying resin (or blend of resin and antioxidant) was fed as a dry powder to open ports at barrels 3 and 5 using a K-TRON™ gravimetric feeder. After compounding in the TSE, the molten composition was discharged out of the TSE through a Zenith gear pump into a flexible hose and subsequent contacting die for coating on an appropriate backing material.

The wt. % of the individual components comprising these adhesives blends (Examples 1–27) plus Comparative Examples (CE) 1–7 that comprised 100% hydrophilic PAA, Comparative Example 8 that comprised only elastomer and tackifer (no polyacrylate), and Comparative Example 9 that comprised a blend of nonhydrophilic polyacrylate, elastomer, and tackifier are provided in Table 2.

TABLE 2

Adhesive Blends

| Ex. No. | Hydrophilic PAA | Wt. % | Elastomer | Wt. % | Tackifier | Wt. % |
|---|---|---|---|---|---|---|
| CE-1 | PAA-1 | 100 | — | 0 | — | 0 |
| 1 | PAA-1 | 80 | Kraton D1107 | 10 | Escorez 1310LC | 10 |
| 2 | PAA-1 | 60 | Kraton D1107 | 20 | Escorez 1310LC | 20 |
| 3 | PAA-1 | 40 | Kraton D1107 | 30 | Escorez 1310LC | 30 |
| CE-2 | PAA-3 | 100 | — | 0 | — | 0 |
| 4 | PAA-3 | 80 | Kraton D1107 | 10 | Escorez 1310LC | 10 |
| 5 | PAA-3 | 60 | Kraton D1107 | 20 | Escorez 1310LC | 20 |
| 6 | PAA-3 | 40 | Kraton D1107 | 30 | Escorez 1310LC | 30 |
| CE-3 | PAA-2 | 100 | — | 0 | — | 0 |
| 7 | PAA-2 | 80 | Natsyn 2210 | 12 | Wingtack 95 | 8 |
| 8 | PAA-2 | 50 | Natsyn 2210 | 30 | Wingtack 95 | 20 |
| 9 | PAA-2 | 20 | Natsyn 2210 | 48 | Wingtack 95 | 32 |
| CE-4 | PAA-4 | 100 | — | 0 | — | 0 |
| 10 | PAA-4 | 80 | Natsyn 2210 | 12 | Wingtack 95 | 8 |
| 11 | PAA-4 | 50 | Natsyn 2210 | 30 | Wingtack 95 | 20 |
| 12 | PAA-4 | 20 | Natsyn 2210 | 48 | Wingtack 95 | 32 |

TABLE 2-continued

Adhesive Blends

| Ex. No. | Hydrophilic PAA | Wt. % | Elastomer | Wt. % | Tackifier | Wt. % |
|---|---|---|---|---|---|---|
| 13 | PAA-2 | 80 | Kraton D1107 | 10 | Escorez 1310LC | 10 |
| 14 | PAA-2 | 80 | Natsyn 2210 | 12 | Wingtack 95 | 8 |
| 15 | PAA-3 | 80 | Kraton D1107 | 10 | Escorez 1310LC | 10 |
| 16 | PAA-3 | 80 | Natsyn 2210 | 12 | Wingtack 95 | 8 |
| CE-5 | PAA-5 | 100 | — | 0 | — | 0 |
| 17 | PAA-5 | 80 | Kraton D1107 | 10 | Escorez 1310LC | 10 |
| 18 | PAA-5 | 80 | Natsyn 2210 | 12 | Wingtack 95 | 8 |
| 19 | PAA-6 | 50 | IR305 | 25 | Escorez I310LC* | 25 |
| 20 | PAA-6 | 75 | IR305 | 12.5 | Escorez 1310LC* | 12.5 |
| 21 | PAA-7 | 50 | IR305 | 25 | Escorez 1310LC* | 25 |
| 22 | PAA-6 | 60 | Kraton D1107 | 20 | Escorez 1310LC | 20 |
| 23 | PAA-6 | 40 | Kraton D1107 | 30 | Escorez 1310LC | 30 |
| CE-6 | PAA-8 | 100 | Kraton D1113 | 0 | Escorez 1310LC | 0 |
| 24 | PAA-8 | 25 | Kraton D1113 | 37.5 | Escorez 1310LC* | 37.5 |
| 25 | PAA-8 | 40 | Kraton D1113 | 30 | Escorez 1310LC* | 30 |
| CE-7 | PAA-9 | 100 | Kraton D1113 | 0 | Escorez 1310LC | 0 |
| 26 | PAA-9 | 25 | Kraton D1113 | 37.5 | Escorez 1310LC* | 37.5 |
| 27 | PAA-9 | 40 | Kraton D1113 | 30 | Escorez 1310LC* | 30 |
| CE-8 | — | 0 | IR305 | 50 | Escorez 1310LC* | 50 |
| CE-9 | CA-1 | 65 | Kraton D1107 | 17.5 | Escorez 1310LC* | 17.5 |

*Examples 19, 20, 21, 24–27, CE-8, and CE-9 included IRGANOX ™ 1010 antioxidant (1.0 wt. %) pre-blended with the tackifier component.

EXAMPLES 28–33 and

Comparative Examples 10–11

Adhesive Blends Prepared by Hot Melt Process

The adhesive blends of Examples 28–33 were prepared by combining together hydrophilic PAA, elastomer, and tackifier components as described for Examples 1–27, except for the following. The Bonnot extruder temperatures were controlled between 79–95° C. The elastomer component was dry fed into an open port of barrel 1 of the TSE, the tackifying resin was fed as a 30/70 split (by weight) into open ports at barrels 3 and 5, respectively, and the acrylic pouches of hydrophilic PAA were melted, masticated, and fed into barrel 9 of the TSE.

The wt. % of the individual components comprising these adhesive blends (Examples 28–33) plus Comparative Example CE-10 that comprised only elastomer and tackifier (no polyacrylate) and Comparative Example CE-11 that comprised 100% hydrophilic PAA are provided in Table 3.

TABLE 3

Adhesive Blends

| Ex. No. | Hydro-philic PAA | wt. % | Elastomer | Wt. % | Tackifier | Wt. % |
|---|---|---|---|---|---|---|
| CE-10 | PAA-10 | 0 | Elastomer A | 55.0 | Escorez 1310LC | 45.0 |
| 28 | PAA-10 | 30 | Elastomer A | 38.5 | Escorez 1310LC | 31.5 |
| 29 | PAA-10 | 50 | Elastomer A | 27.5 | Escorez 1310LC | 22.5 |
| 30 | PAA-10 | 70 | Elastomer A | 16.5 | Escorez 1310LC | 13.5 |
| 31 | PAA-10 | 30 | Elastomer A | 40.6 | Escorez 1310LC | 29.4 |
| 32 | PAA-10 | 30 | Elastomer A | 36.4 | Escorez 1310LC | 33.6 |
| 33 | PAA-10 | 30 | Elastomer A | 35.0 | Escorez 1310LC | 28.0 |
| CE-11 | PAA-10 | 100 | — | 0 | — | 0 |

EXAMPLES 34–41 and

Comparative Example 12

Adhesive Blends Prepared by Hot Melt Process

The adhesive blends of Examples 34–41 were prepared by combining together hydrophilic PAA, elastomer, and tackifier components as described for Examples 28–33, except that a compatibilizing agent was optionally blended with the first part of the tackifier resin (30%) and added into an open port at barrel 3 of the TSE.

The wt. % of the individual components comprising these adhesives blends (Examples 34–41) plus Comparative Example CE-12 that comprised 100% hydrophilic PAA are provided in Table 4.

TABLE 4

Adhesive Blends

| Ex. No. | Hydro-philic PAA | Wt. % | Elastomer | Wt. % | Tackifier + Compatibilizer | Wt. % |
|---|---|---|---|---|---|---|
| CE-12 | PAA-11 | 100.0 | — | 0 | — | 0 |
| 34 | PAA-11 | 50.0 | Elastomer A | 27.5 | Escorez 1310LC | 22.5 |
| 35 | PAA-11 | 49.8 | Elastomer A | 27.4 | Escorez 1310LC +<br>COMP A | 22.4<br>0.5 |
| 36 | PAA-11 | 49.5 | Elastomer A | 27.2 | Escorez 1310LC +<br>COMP A | 22.3<br>1.0 |
| 37 | PAA-11 | 48.5 | Elastomer A | 26.7 | Escorez 1310LC +<br>COMP A | 21.8<br>3.0 |
| 38 | PAA-11 | 47.0 | Elastomer A | 25.9 | Escorez 1310LC +<br>COMP A | 21.2<br>6.0 |
| 39 | PAA-11 | 50.0 | Elastomer A | 27.5 | Escorez 1310LC +<br>COMP B | 22.5<br>0.5 |
| 40 | PAA-11 | 49.5 | Elastomer A | 27.2 | Escorez 1310LC +<br>COMP B | 22.3<br>1.0 |
| 41 | PAA-11 | 48.5 | Elastomer A | 26.7 | Escorez 1310LC +<br>COMP B | 21.8<br>3.0 |

EXAMPLES 42–53 and

Comparative Examples 13–17

Taffeta Backing Coated with Adhesive Blends

The adhesive blends of Examples 1–12 and comparative adhesive samples CE-1 to CE-4 and CE-9 (molten materials as listed in Table 2) were coated onto an acetate taffeta backing. Coating conditions involved setting the gear pump, flexible hose and coating die to the same temperature that was in the range of 149–184° C. the gear pump and film take-away speeds were adjusted to provide a coating weight of 58 g/m$^2$. The backing was a 180×48 plain weave acetate taffeta cloth, 75-denier fiber in the warp direction, 150-denier fiber in the weft direction as available from Milliken & Co., Spartanburg, Ga.

Samples of the resulting adhesive-coated backings were evaluated for adhesion to steel, initial ($T_0$) adhesion to wet and dry skin, adhesion to skin after 48 hours ($T_{48}$), MVTR, and porosity. The test results for Examples 42–53 (backing coated with adhesive blends) are provided in Table 5 and are compared to Comparative Examples 13–16 (backing coated only with hydrophilic polyacrylate adhesive) and Comparative Example 17 (backing coated with a polyacrylate/elastomer/tackifier blend made with the nonhydrophilic polyacrylate PSA CA-1).

TABLE 5

Taffeta Backing Coated with Adhesive Blends

| Ex. No. | Adhesive Ex. No. | Adhesion to Steel (N/dm) | Adhesion to Skin (N/dm) $T_0$ Wet | $T_0$ Dry | $T_{48}$ | MVTR (g/m$^2$/24 hr) | Porosity (sec) |
|---|---|---|---|---|---|---|---|
| CE-13 | CE-1 | 13 | 2.9 | 0.2 | 2.5 | 1660 | 77 |
| 42 | 1 | 32 | 2.4 | 0.8 | 4.7 | 1350 | 86 |
| 43 | 2 | 43 | NA | 2.7 | 5.4 | 550 | 102 |
| 44 | 3 | 47 | NA | 3.1 | 3.1 | 160 | 77 |
| CE-14 | CE-2 | 9 | 2.4 | 0.1 | 2.5 | 1200 | 161 |
| 45 | 4 | 39 | 2.9 | 0.7 | 5.6 | 1210 | 72 |
| 46 | 5 | 46 | NA | 2.2 | 5.3 | 450 | 287 |
| 47 | 6 | 54 | NA | 3.0 | 2.8 | 150 | 300 |
| CE-15 | CE-3 | 15 | 3.3 | 0.2 | 2.5 | 1800 | 219 |
| 48 | 7 | 20 | 3.3 | 0.5 | 5.3 | 1610 | 195 |
| 49 | 8 | 20 | NA | 1.8 | 7.5 | 1100 | 300 |
| 50 | 9 | 9 | NA | 3.7 | 7.4 | 330 | 197 |
| CE-16 | CE-4 | 10 | 2.2 | 0.1 | 1.9 | 1830 | 90 |
| 51 | 10 | 25 | 2.9 | 0.5 | 4.9 | 1560 | 211 |
| 52 | 11 | 13 | NA | 2.5 | 7.6 | 900 | 200 |
| 53 | 12 | 7 | NA | 5.3 | 8.0 | 380 | 168 |
| CE-17 | CE-9 | 15 | 1.4 | 2.5 | 9.8 | 320 | 149 |

The results from Table 5 show that the taffeta backings coated with adhesive blends of the invention (e.g., Examples 42, 45, 48, and 51) possessed great dry skin adhesion with little or no loss in wet skin adhesion when compared to backings coated only with a hydrophilic wet-stick polyacrylate adhesive (Comparative Examples CE-13 to CE-16). Compared to the backing coated with an adhesive blend of nonhydrophilic polyacrylate/elastomer/tackifier (Comparative Example CE-17), backings coated with adhesive blends of the invention possessed significantly greater wet skin adhesion.

EXAMPLES 54–59 and

Comparative Examples 18–20

Nonwoven Rayon Backing Coated with Adhesive Blends

The adhesive blends of Examples 13–18 and comparative adhesive samples CE-2, CE-3 and CE-5 (molten materials as listed in Table 2) were coated onto a nonwoven rayon backing. Coating conditions involved setting the gear pump, flexible hose and coating die to the same temperature that was in the range of 142–163° C. The gear pump and film take-away speeds were adjusted to provide a coating weight of 25 g/m$^2$. The backing was formed from an embossed polyester-rayon carded web as described in Example 3 of U.S. patent application Ser. No. 09/367,509.

Samples of the resulting adhesive-coated backings were evaluated for adhesion to steel, initial ($T_0$) adhesion to wet and dry skin, adhesion to skin after 24 hours ($T_{24}$), MVTR, and porosity. The test results for Examples 54–59 (backing coated with adhesive blends) are provided in Table 6 and are compared to Comparative Examples 18–20 (backing coated only with hydrophilic polyacrylate adhesive) and the commercial MICROPORE™ medical tape (3M Co., St. Paul, Minn.).

TABLE 6

Nonwoven Rayon Backing Coated with Adhesive Blends

| Ex. No. | Adhesive Ex. No. | Adhesion to Steel (N/dm) | Adhesion to Skin (N/dm) $T_0$ Wet | $T_0$ Dry | $T_{48}$ | MVTR (g/m$^2$/24 hr) | Porosity (sec) |
|---|---|---|---|---|---|---|---|
| CE-18 | CE-3 | 20 | 3.7 | 1.3 | 2.4 | 3340 | 5 |
| 54 | 13 | 23 | 1.2 | 2.1 | 5.3 | 1220 | 300 |
| 55 | 14 | 18 | 4.6 | 2.6 | 4.7 | 2610 | 32 |
| CE-19 | CE-2 | 18 | 2.3 | 1.0 | 2.4 | 4780 | 2 |
| 56 | 15 | 25 | 1.6 | 1.9 | 5.5 | 1330 | 393 |
| 57 | 16 | 16 | 3.8 | 1.9 | 4.9 | 2660 | 8 |
| CE-20 | CE-5 | 22 | 4.0 | 1.1 | 3.1 | 2500 | 13 |
| 58 | 17 | 21 | 1.6 | 1.9 | 4.7 | 1380 | 300 |
| 59 | 18 | 19 | 2.9 | 1.7 | 4.0 | 2400 | 253 |
| MICROPORE | — | 10 | 1.8 | 1.1 | 4.7 | 3910 | 1 |

The results from Table 6 show that the nonwoven rayon backings coated with adhesive blends of the invention (Examples 54–59) possessed greater dry skin adhesion and maintained adequate wet skin adhesion when compared to backings coated only with a hydrophilic wet-stick polyacrylate adhesive (Comparative Examples CE-18 to CE-20) or compared to the commercial MICROPORE™ medical tape.

EXAMPLES 60–70 and

Comparative Examples 21–23

Woven Cotton Cloth Backing Coated with Adhesive Blends

The adhesive blends of Examples 19–27 and comparative adhesive samples CE-6 to CE-8 (molten materials as listed in Table 2) were coated onto a woven bleached cotton cloth backing with a non-wick finish (Weave No. 63×46 or No. 63–54, Aurora Textile Finishing Company, Catawba, N.C.). Coating conditions involved setting the gear pump, flexible hose and coating die to the same temperature that was in the range of 120–140° C. The gear pump and film take-away speeds were adjusted to provide a coating weight of 62–74 g/m$^2$.

Samples of the resulting adhesive-coated backings were evaluated for adhesion to steel, initial ($T_0$) adhesion to wet and dry skin, adhesion to skin after 24 hours ($T_{24}$), MVTR, and porosity. The test results for Examples 60–70 (backing coated with adhesive blends) are provided in Table 7 and are compared to Comparative Examples 21–22 (backings coated only with hydrophilic polyacrylate adhesives) and Comparative Example 23 (backing coated only with elastomer and tackifier).

TABLE 7

Woven Cotton Cloth Backing Coated with Adhesive Blends

| Ex. No. | Adhesive Ex. No. | Adhesion to Steel (N/dm) | Adhesion to Skin (N/dm) $T_0$ Wet | o Dry | $T_{24}$ | MVTR (g/m²/ 24 hr) | Porosity (sec) |
|---|---|---|---|---|---|---|---|
| 60 | 19 | 24 | 3.7 | 4.7 | 4.6 | 7000 | 1 |
| 61* | 19 | 31 | 5.2 | 5.7 | 6.6 | 6170 | 1 |
| 62* | 20 | 21 | 7.4 | 5.2 | 5.1 | 3250 | 4 |
| 63* | 21 | 31 | 4.4 | 4.4 | 6.7 | 7200 | 1 |
| 64 | 21 | 25 | 4.4 | 7.9 | 7.4 | 6880 | 2 |
| 65 | 22 | 33 | 1.6 | 1.6 | 9.0 | 3180 | 23 |
| 66 | 23 | 42 | 0.8 | 2.4 | 7.0 | 5460 | 5 |
| CE-21 | CE-6 | 6.4 | 3.2 | 1.4 | 0.9 | 7983 | 0.2 |
| 67 | 24 | 37.1 | 2.5 | 3.2 | 5.1 | 4698 | 8.2 |
| 68 | 25 | 29 | 2.9 | 3.6 | 5.2 | 5613 | 9 |
| CE-22 | CE-7 | 35.6 | 3.3 | 2.0 | 4.7 | 6387 | 0.4 |
| 69 | 26 | 84.6 | 2.4 | 2.7 | 4.9 | 6245 | 1.5 |
| 70 | 27 | 90 | 2.5 | 3.3 | 6.8 | 5513 | 4.4 |
| CE-23* | CE-8 | 30 | 9.6 | 14.1 | 13.9 | 7990 | 1 |

*Examples 61, 62, 63 and CE-23 were post-coating irradiated with E-beam radiation at a level of 2 Mrad dosage at 175 kV directly after and in-line with the coating process using an ELECTOCURTAIN ™ CB-175 electron beam system (Energy Sciences, Inc., Wilmington, MA).

The results from Table 7 show that the cotton cloth backings coated with adhesive blends of the invention (Examples 60–70) possessed generally greater dry skin adhesion and maintained adequate wet skin adhesion when compared to backings coated only with a hydrophilic wet-stick polyacrylate adhesive (Comparative Examples CE-21 to CE-22) and possessed much more desirable initial (wet and dry) and 24-hour skin adhesion values than a backing coated only with a tackified elastomer (no hydrophilic polyacrylate) adhesive (Comparative Example CE-23). The more desirable skin adhesion values of the present invention examples show good adhesion to both wet and dry skin, while not having the undesirably high levels of wet and dry skin adhesion possessed by Comparative Example 23.

EXAMPLE 71–76 and

Comparative Examples 24–25

Polycoated Rayon Cloth Backing Coated with Adhesive Blends

The adhesive blends of Examples 28–33 and comparative adhesive samples CE-10 and CE-11 (molten materials as listed in Table 3) were coated onto a polycoated rayon cloth backing. Coating conditions involved setting the gear pump, flexible hose and coating die to the same temperature that was in the range of 160–170° C. The gear pump and film take-away speeds were adjusted to provide a coating weight of 126 g/m² and a dry coating thickness of 19.7 micrometers. The backing was a rayon cloth laminated with polyethylene (40×30 thread count, No. 30 Rayon/70P, Itochu International, Inc. New York, N.Y.). The adhesive sides of all coated backings were irradiated with E-Beam radiation at a level of 4 Mrad at 175 kV using an ELECTROCURTAIN™ CB-300 electron beam system (Energy Sciences, Inc.)

Samples of the resulting adhesive-coated backings were evaluated for two-bond adhesion, peel adhesion to stainless steel, shear to SS, peel adhesion to glass (21° and 4° C. samples), and under-water peel adhesion to SS (1.0-minute and 960-minute dwell times). The test results for Examples 71–76 (backing coated with adhesive blends) are provided in Table 8 and are compared to Comparative Example 24 (backing coated only with elastomer and tackifier) and 25 (backing coating only with hydrophilic polyacrylate adhesive).

TABLE 8

Polycoated Rayon Cloth Backing Coated with Adhesive Blends

| Ex. No. | Adh. Ex. No. | Two-Bond Adhesion (N/dm) | Stainless Steel (SS) Adh. (N/dm) | Shear (Min) | Adhesion to Glass (N/dm) 21° C. | 4° C. | Under-Water Adhesion to SS (N/dm) 1.0 Min | 960 Min |
|---|---|---|---|---|---|---|---|---|
| CE-24 | CE-10 | 85 | 66 | >5000 | 123 | 59 | 14 | 15 |
| 71 | 28 | 67 | 38 | 124 | 104 | 140 | 30 | 12 |
| 72 | 29 | 44 | 26 | 61 | 77 | 134 | 35 | 49 |
| 73 | 30 | 35 | 34 | 59 | 72 | 138 | 59 | 65 |
| 74 | 31 | 50 | 31 | 82 | 67 | 136 | 32 | 18 |
| 75 | 32 | 62 | 53 | 163 | 105 | 89 | 33 | 19 |
| 76 | 33 | 79 | 40 | 118 | 92 | 143 | 34 | 25 |
| CE-25 | CE-11 | 27 | 32 | 62 | 62 | 100 | 50 | 53 |

The results from Table 8 show that the comparative tape sample (CE-24) made from an adhesive (CE-10) containing only elastomer and tackifier components had high dry adhesion and excellent shear, but very poor wet (under-water) adhesion because of its hydrophobic nature. The comparative tape sample (CE-25) made from the hydrophilic wet-stick polyacrylate adhesive (CE-11) had good wet adhesion, but generally low two-bond adhesion, peel adhesion and poor shear. In contrast, the cloth backings coated with the adhesive blends of the invention (Examples 71–76) showed significantly improved wet adhesion versus CE-24 and generally had improved two-bond adhesion, dry adhesion, and shear holding power versus CE-25.

EXAMPLES 77–84 and

Comparative Example 26

Polyester Film Backing Coated with Adhesive Blends

The adhesive blends of Examples 34–41 and comparative adhesive sample CE-12 (molten materials as listed in Table 4) were coated onto a polyester film backing. Coating conditions involved setting the gear pump, flexible hose and coating die to the same temperature that was in the range of 160–170° C. The gear pump and film take-away speeds were adjusted to provide a coating weight of 126 g/m² and a dry coating thickness of 19.7 micrometers. The backing was a 1.5-mil polyester (PET) film that was corona treated on both sides and treated on one side with an acrylic-polyurethane low adhesion backsize (LAB) before coating with the adhesive.

Samples of the resulting adhesive-coated backings were evaluated for peel adhesion to stainless steel, shear to SS, peel adhesion to glass (21° C. and 4° C. samples), and under-water peel adhesion to SS (1.0-minute and 960-minute dwell times). The test results for Examples 77–84 (backing coated with adhesive blends) are provided in Table 9 and are compared to Comparative Example 26 (backing coated only with hydrophilic polyacrylate adhesive).

TABLE 9

Polyester Film Backing Coated with Adhesive Blends

| Ex. No. | Adh. Ex. No. | Two Bond Adhesion (N/dm) | Stainless Steel (SS) Adh. (N/dm) | Stainless Steel (SS) Shear (Min) | Adhesion to Glass (N/dm) 21° C. | Adhesion to Glass (N/dm) 4° C. | Under-Water Adhesion to SS (N/dm) 1.0 Min | Under-Water Adhesion to SS (N/dm) 960 Min |
|---|---|---|---|---|---|---|---|---|
| CE-26 | CE-12 | 23 | 34 | 28 | 67 | >164* | 77 | >164* |
| 77 | 34 | 59 | 44 | 365 | 85 | 181 | 33 | >164* |
| 78 | 35 | 51 | 39 | 250 | 82 | 184 | 28 | >164* |
| 79 | 36 | 45 | 34 | 314 | 88 | 197 | 21 | >164* |
| 80 | 37 | 40 | 24 | 1224 | 76 | 166 | 28 | >164* |
| 81 | 38 | 23 | 24 | >5000 | 58 | 169 | 20 | 153 |
| 82 | 39 | 43 | 46 | 256 | 155 | 155 | 18 | >164* |
| 83 | 40 | 39 | 35 | 358 | 160 | 160 | 31 | >164* |
| 84 | 41 | 24 | 23 | >5000 | 106 | 106 | 27 | 121 |

*>164 = Adhesion value exceeded 164 N/dm and backing broke.

The results from Table 9 show that the comparative tape sample (CE-26) made from the hydrophilic wet-stick polyacrylate adhesive (CE-12) had good wet adhesion, but generally low two-bond adhesion, peel adhesion and poor shear. In contrast, the polyester film backings coated with the adhesive blends of the invention (Examples 77–84) generally showed improved two-bond adhesion, dry adhesion, and shear holding power versus CE-26.

Various modifications and alterations of this invention will become apparent to those skilled in the art without departing from the scope and principles of this invention, and it should be understood that this invention is not to be unduly limited to the illustrative embodiments set forth hereinabove. All publications and patents are incorporated herein by reference to the same extent as if each individual publication or patent was specifically and individually indicated to be incorporated by reference.

What is claimed is:

1. An adhesive composition comprising a blend of (I) a hydrophilic pressure sensitive adhesive, wherein the hydrophilic pressure sensitive adhesive comprises
  (i) a polymerization product of:
    (a) about 15 to about 85 parts by weight of an (meth)acrylate ester monomer wherein the (meth) acrylate ester monomer, when polymerized, has a glass transition temperature ($T_g$) of less than about 10° C.;
    (b) about 85 to about 15 parts by weight of a hydrophilic acidic comonomer; and
    (c) at least about 10 parts based on 100 parts of the sum of components (a)+(b) of a non-reactive plasticizing agent; and (II) a hydrophobic pressure sensitive adhesive.

2. The adhesive composition according to claim 1 wherein the blend comprises (I) 5-95 parts by weight of the hydrophilic pressure sensitive adhesive and (II) 95-5 parts by weight of the hydrophobic pressure sensitive adhesive.

3. The adhesive composition according to claim 1 wherein the hydrophobic pressure sensitive adhesive is an elastomer or thermoplastic elastomer.

4. The adhesive composition according to claim 1 wherein the initial peel adhesion ($T_0$) to wet or dry skin is at least 0.8 N/dm and not greater than 15 N/dm.

5. The adhesive composition according to claim 1 wherein the initial peel adhesive to stainless steel underwater is at least 16 N/dm and the two-bond is at least 25 N/dm.

6. The adhesive composition according to claim 1 further comprising antimicrobial compositions or antioxidant compositions.

7. An adhesive composition comprising a blend of:

(I) a hydrophilic pressure sensitive adhesive, wherein the hydrophilic pressure sensitive adhesive comprises
  (i) a polymerization product of:
    (a) about 15 to about 85 parts by weight of an (meth)acrylate ester monomer wherein the (meth) acrylate ester monomer, when polymerized, has a glass transition temperature ($T_g$) of less than about 10° C.;
    (b) about 85 to about 15 parts by weight of a hydrophilic acidic comonomer; and
    (c) at least about 10 parts based on 100 parts of the sum of components (a)+(b) of a non-reactive plasticizing agent; and (II) a hydrophobic pressure sensitive adhesive, wherein the hydrophobic pressure sensitive adhesive is an elastomer or thermoplastic elastomer.

8. The adhesive composition according to claim 7 wherein the polymerization product further comprises (d) a residue of a polymerization initiator.

9. The adhesive composition according to claim 7 wherein the hydrophobic pressure sensitive adhesive is a non-tacky elastomer or thermoplastic elastomer and a tackifying resin or plasticizer.

10. The adhesive composition according to claim 7 wherein the hydrophobic pressure sensitive adhesive is a tacky elastomer or thermoplastic elastomer and optionally, a tackifying resin or plasticizer.

11. The adhesive composition according to claim 7 wherein the hydrophilic pressure sensitive adhesive is the polymerization product of (a) isooctyl acrylate or 2-ethylhexyl acrylate, (b) acrylic acid, (c) polyethylene glycol, polypropylene glycol, polyethylene glycols, copolymers and derivatives thereof, (d) at least one polymerization initiator, and (e) at least one chain transfer agent.

12. The adhesive composition according to claim 7 wherein the hydrophobic pressure sensitive adhesive is selected from the group consisting of styrene block copolymers of styrene and isoprene, butadiene or ethylene-butylene; polyisoprene; polybutadiene; polyisobutylene; butyl rubber; styrene-butadiene rubber; natural rubber; and poly-α-olefins.

13. The adhesive composition according to claim 12 wherein the hydrophobic pressure sensitive adhesive further comprises a tackifying resin selected from the group consisting of liquid rubbers, aliphatic and aromatic hydrocarbon resins, rosin, natural resins such as dimerized or hydrogenated balsams and esterified abietic acids, polyterpenes, terpene phenolics, phenol-formaldehyde resins, and rosin esters.

14. A method of using the adhesive composition of claim 1 on wet or dry surfaces comprising the steps of:

(a) applying a layer of the adhesive blend to a predetermined thickness onto a substrate, and (b) applying the layered substrate onto a wet or dry surface.

15. The method according to claim 14, wherein the step of applying the layered substrate comprises applying the layered substrate to wet or dry skin.

16. The method according to claim 14, wherein the substrate is selected from the group consisting of films, foams, wovens, nonwovens, knits, and laminates thereof.

17. A pressure sensitive adhesive article comprising a substrate and a pressure sensitive adhesive composition disposed thereon, wherein the pressure sensitive adhesive composition comprises a blend of:

(I) a hydrophilic pressure sensitive adhesive, wherein the hydrophilic pressure sensitive adhesive comprises (i) a polymerization product of:

(a) about 15 to about 85 parts by weight of an (meth)acrylate ester monomer wherein the (meth) acrylate ester monomer, when polymerized, has a glass transition temperature ($T_g$) of less than about 10° C.;

(b) about 85 to about 15 parts by weight of a hydrophilic acidic comonomer; and (c) at least about 10 parts based on 100 parts of the sum of components (a)+(b) of a non-reactive plasticizing agent; and (II) a hydrophobic pressure sensitive adhesive.

18. The pressure sensitive adhesive article of claim 17 wherein the substrate is selected from the group of cloth, metallized foil, metallized film, polymeric film, nonwoven polymeric, paper, foam, and combinations thereof.

19. A pressure sensitive adhesive article comprising a substrate and a pressure sensitive adhesive composition disposed thereon, wherein the pressure sensitive adhesive composition comprises a blend of:

(I) a hydrophilic pressure sensitive adhesive, wherein the hydrophilic pressure sensitive adhesive comprises (i) a polymerization product of:

(a) about 15 to about 85 parts by weight of an (meth)acrylate ester monomer wherein the (meth) acrylate ester monomer, when polymerized, has a glass transition temperature ($T_g$) of less than about 10° C.;

(b) about 85 to about 15 parts by weight of a hydrophilic acidic comonomer; and (c) at least about 10 parts based on 100 parts of the sum of components (a)+(b) of a non-reactive plasticizing agent; and (II) a hydrophobic pressure sensitive adhesive, wherein the hydrophobic pressure sensitive adhesive is an elastomer or thermoplastic elastomer.

20. The pressure sensitive adhesive article of claim 19 wherein the substrate is selected from the group of cloth, metallized foil, metallized film, polymeric film, nonwoven polymeric material, paper, foam, and combinations thereof.

21. The adhesive composition according to claim 1, wherein the non-reactive plasticizing agent is present in an amount of about 15 to 100 parts based on 100 parts of the sum of components (a)+(b).

22. The adhesive composition according to claim 1, wherein the non-reactive plasticizing agent is polyethylene oxide; polypropylene oxide; polyethylene glycol; a copolymer of ethylene oxide, propylene oxide or polyethylene glycol; an alkyl or aryl functionalized polyalkylene oxide; a phenyl ether of polyethylene oxide; a benzoyl functionalized polyether; a polypropylene glycol dibenzoate; a monomethyl ether of polyethylene oxide; a methoxypolyethylene glycol; a polypropylene glycol; an ethylene oxide/propylene oxide block copolymer; or a mixture thereof.

23. The adhesive composition according to claim 7, wherein the non-reactive plasticizing agent is present in an amount of about 15 to 100 parts based on 100 parts of the sum of components (a)+(b).

24. The adhesive composition according to claim 7, wherein the non-reactive plasticizing agent is polyethylene oxide; polypropylene oxide; polyethylene glycol; a copolymer of ethylene oxide, propylene oxide or polyethylene glycol; an alkyl or aryl functionalized polyalkylene oxide; a phenyl ether of polyethylene oxide; a benzoyl functionalized polyether; a polypropylene glycol dibenzoate; a monomethyl ether of polyethylene oxide; a methoxypolyethylene glycol; a polypropylene glycol; an ethylene oxide/propylene oxide block copolymer; or a mixture thereof.

25. The adhesive composition according to claim 17, wherein the hydrophobic pressure sensitive adhesive is an elastomer or thermoplastic elastomer.

26. The adhesive composition according to claim 17, wherein the hydrophobic pressure sensitive adhesive is the polymerization product of (a) isooctyl acrylate or 2-ethylhexyl acrylate, (b) acrylic acid, (c) a non-reactive plasticizer selected from the group consisting of polyethylene glycol, polypropylene glycol, polyethylene glycols, copolymers and derivatives thereof, (d) at least one polymerization initiator, and (e) at least one chain transfer agent.

27. The adhesive composition according to claim 17, wherein the hydrophobic pressure sensitive adhesive is selected from the group consisting of styrene block copolymers of styrene and isoprene, butadiene or ethylene-butylene; polyisoprene; polybutadiene; polyisobutylene; butyl rubber; styrene-butadiene rubber; natural rubber; and poly-$\alpha$-olefins.

28. The adhesive composition according to claim 17, wherein the non-reactive plasticizing agent is present in an amount of about 15 to 100 parts based on 100 parts of the sum of components (a)+(b).

29. The adhesive composition according to claim 17, wherein the non-reactive plasticizing agent is polyethylene oxide; polypropylene oxide; polyethylene glycol; a copolymer of ethylene oxide, propylene oxide or polyethylene glycol; an alkyl or aryl functionalized polyalkylene oxide; a phenyl ether of polyethylene oxide; a benzoyl functionalized polyether; a polypropylene glycol dibenzoate; a monomethyl ether of polyethylene oxide; a methoxypolyethylene glycol; a polypropylene glycol; an ethylene oxide/propylene oxide block copolymer; or a mixture thereof.

30. The adhesive composition according to claim 19, wherein the non-reactive plasticizing agent is present in an amount of about 15 to 100 parts based on 100 parts of the sum of components (a)+(b).

31. The adhesive composition according to claim 19, wherein the non-reactive plasticizing agent is polyethylene oxide; polypropylene oxide; polyethylene glycol; a copolymer of ethylene oxide, propylene oxide or polyethylene glycol; an alkyl or aryl functionalized polyalkylene oxide; a phenyl ether of polyethylene oxide; a benzoyl functionalized polyether; a polypropylene glycol dibenzoate; a monomethyl ether of polyethylene oxide; a methoxypolyethylene glycol; a polypropylene glycol; an ethylene oxide/propylene oxide block copolymer; or a mixture thereof.

* * * * *

UNITED STATES PATENT AND TRADEMARK OFFICE

CERTIFICATE OF CORRECTION

PATENT NO. : 6,497,949 B1
DATED : December 24, 2002
INVENTOR(S) : Hyde, Patrick D.

It is certified that error appears in the above-identified patent and that said Letters Patent is hereby corrected as shown below:

Column 4,
Line 40, insert a period after the the word "thereof".

Column 6,
Line 12, insert a period after the word "thereof".

Column 7,
Line 28, after the word "copolymerization" add -- of --.

Column 19,
Line 12, "the gear pump" should read -- The gear pump --.

Column 20,
Line 40, "polymeric, paper," should read -- polymeric material, paper, --.

Signed and Sealed this

Eighth Day of July, 2003

JAMES E. ROGAN
*Director of the United States Patent and Trademark Office*